United States Patent [19]

Kahle, II et al.

[11] Patent Number: 5,091,451
[45] Date of Patent: Feb. 25, 1992

[54] REACTION PRODUCTS OF ALPHA-AMINOMETHYLENE PHOSPHONIC ACIDS AND EPOXY COMPOUNDS AND THEIR USE IN COATING COMPOSITIONS

[75] Inventors: Charles F. Kahle, II, Allison Park; Kurt G. Olson, Gibsonia; James A. Claar, Export; Paul H. Pettit, Jr., Wexford; Paul R. Kerr, Allison Park, all of Pa.

[73] Assignee: PPG Industries, Inc., Pittsburgh, Pa.

[21] Appl. No.: 663,354

[22] Filed: Mar. 4, 1991

Related U.S. Application Data

[62] Division of Ser. No. 333,355, Apr. 3, 1989, Pat. No. 5,034,556.

[51] Int. Cl.$^5$ ............................................. C08K 5/17
[52] U.S. Cl. ..................................... 524/124; 524/441
[58] Field of Search ........................................ 524/124

[56] References Cited

U.S. PATENT DOCUMENTS

| | | | |
|---|---|---|---|
| 3,269,812 | 8/1966 | Irani et al. | 252/153 |
| 3,956,199 | 5/1976 | Dawson et al. | 252/545 |
| 4,051,110 | 9/1977 | Quinlan | 260/72 R |
| 4,621,112 | 11/1986 | Backhouse et al. | 524/145 |
| 4,717,424 | 1/1988 | Wilfinger et al. | 106/308 |

FOREIGN PATENT DOCUMENTS

| | | |
|---|---|---|
| 1276822 | 6/1972 | United Kingdom . |
| 2138424 | 10/1984 | United Kingdom . |

OTHER PUBLICATIONS

Helmut Blum and Peter Christophliemk, "Technical Aminopolymethylenephosphonic acids as scale inhibitors", pp. 108–114, *Phosphorus and Sulfur* 30 (1987) 619.
Phosphates Division of Albright & Wilson, Ltd., 'Briquest' Phosphonates as Sequestrants and Surfactants, pp. 1–4, Product Technical Information.
Phosphates Division of Albright & Wilson, Ltd., "Briquest ADPA-60A", Acetodiphosphonic acid aqueous solution, 2 sheets.
Monsanto Company, "Dequest 2000 and 2006 Phosphonates", Technical Bulletin No. IC/WT-101, 5 sheets.
Monsanto Company, "Dequest 2041 and 2051 Phosphonates", 7 sheets.
Monsanto Company, "Dequest 2060 Organophosphorus Product", Technical Bulletin No. IC/SCS-322, 3 sheets.
Albright & Wilson Inc., "Organophosphorus Chemicals, 1 sheet; Flame Retardants, 2 sheets; Surfactants, 2 sheets; Functional Fluid Additives and Precursors, 2 sheets; Sequestrants, Corrosion and Scale Inhibitors, 1 sheet; Lubricant Additives, 1 sheet; Inorganic Chemicals, 2 sheets; Proprietary Metal Finishing Processes, 1 sheet; and Products by Industry", 2 sheets.
Alfred Bader, "How to Find a Great Herbicide", *Aldrichimica Acta*, vol. 21, No. 1, 1988.

*Primary Examiner*—Paul R. Michl
*Assistant Examiner*—Edward J. Cain
*Attorney, Agent, or Firm*—William J. Uhl

[57] ABSTRACT

The disclosure is directed to a compound which is a reaction product of at least one phosphonic acid group of an alpha-aminomethylene phosphonic acid containing at least one group corresponding to the formula,

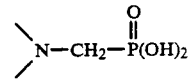

with an epoxy group of a compound containing at least one epoxy group.

The disclosure is also directed to waterborne coating compositions, organic solvent-borne coating compositions, and powder coating compositions containing the aforesaid reaction product.

16 Claims, No Drawings

REACTION PRODUCTS OF ALPHA-AMINOMETHYLENE PHOSPHONIC ACIDS AND EPOXY COMPOUNDS AND THEIR USE IN COATING COMPOSITIONS

This is a division of application Ser. No. 07/333,355, filed Apr. 3, 1989 now U.S. Pat. No. 5,034,556.

BACKGROUND OF THE INVENTION

This invention is directed to compounds which are reaction products of alpha-aminomethylene phosphonic acids and epoxy compounds and to their use in coating compositions.

U.S. Pat. No. 4,621,112 is directed to the use of an organic ester of orthophosphoric acid, which ester is the reaction product as specified of a compound containing a —O—$PO_3H_2$ group with a compound containing an epoxide group, to help prevent the evolution of gas (alternately referred to in the present application as "gassing") by the reaction of metallic pigment with the aqueous phase of a waterborne coating composition. While the use of such organic esters of orthophosphoric acid may help meet the object of providing an antigassing additive for such waterborne coating compositions, a number of disadvantages have been found with respect to such use. For example, it has been found that dry films produced from waterborne coating compositions which incorporate such art known compounds tend to be deficient in humidity resistance. Moreover, their effectiveness as antigassing agents is not entirely satisfactory.

The present invention is directed to a new class of compounds which not only reduce or prevent gassing of waterborne coating compositions containing metallic pigment better than the aforesaid art known organic esters of orthophosphoric acid, but, among other advantages, do not disadvantageously hurt humidity resistance of dry films produced therefrom compared to such art known organic esters of orthophosphoric acid. Moreover, the present invention is also directed to the use of this new class of compounds in organic solvent-borne coating compositions containing organic coloring pigment to improve the color stability of such solvent-borne coating compositions. Additionally, the present invention is directed to the use of this new class of compounds in powder coatings to improve the dispersibility of pigment therein. These and other objects of the invention will become apparent to the reader infra.

SUMMARY OF THE INVENTION

The present invention provides for a compound which is a reaction product of at least one phosphonic acid group of an alpha-aminomethylene phosphonic acid containing at least one group corresponding to the formula,

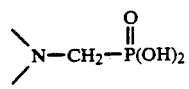

with an epoxy group of a compound containing at least one epoxy group. Typically the alpha-aminomethylene phosphonic acid corresponds to the formula,

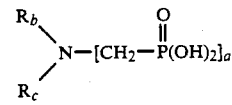

wherein $a=1$, 2 or 3, $a+b+c=3$, and each R, which may be the same or different, is selected from the group consisting of alkyl, aryl, alkaryl, aralkyl and a monovalent residue of a polyether compound.

The present invention also provides for a waterborne coating composition comprising a film-forming polymer, a metallic pigment and an aqueous diluent medium, wherein the tendency of the pigment to react with the aqueous medium and release gaseous material is prevented or reduced by the incorporation in the waterborne coating composition of an effective amount of a compound of the present invention.

The present invention also provides for an organic solvent-borne coating composition comprising a film-forming polymer, a metallic pigment, an organic solvent medium, and a compound of the present invention, particularly such organic solvent-borne coating composition additionally comprising an organic coloring pigment.

Finally, the present invention also provides for a powder coating composition comprising a film-forming polymer and a pigment, wherein dispersibility of said pigment in said powder coating composition is improved by incorporating therein an effective amount of a compound of the present invention.

DETAILED DESCRIPTION OF THE INVENTION

A compound of the invention is a reaction product of at least one phosphonic acid group of an alpha-aminomethylene phosphonic acid containing at least one group corresponding to the formula, $$\phantom{x}\diagdown_{\diagup}N-CH_2-\overset{\overset{O}{\|}}{P}(OH)_2$$

with an epoxy group of a compound containing at least one epoxy group, preferably with an epoxy group of a compound containing at least one 1,2-epoxy group. It will be understood that the two dashes to the left of N in the aforesaid formula represent two valences on N which are, of course, satisfied in the respective alpha-aminomethylene phosphonic acid. Typically, in preferred embodiments of the invention, the alpha-aminomethylene phosphonic acid corresponds to the formula, $$\overset{R_b}{\diagdown}_{\underset{R_c}{\diagup}}N-[CH_2-\overset{\overset{O}{\|}}{P}(OH)_2]_a$$

wherein $a=1$, 2 or 3, preferably $a=2$, $a+b+c=3$, and each R, which may be the same or different, is selected from the group consisting of alkyl, aryl such as phenyl and the like, alkaryl such as tolyl, xylyl or the like, aralkyl such as benzyl, phenethyl and the like, and a monovalent residue of a polyether compound. It is to be understood that alkyl, aryl, alkaryl, and aralkyl groups as used herein are considered to include such groups containing one or more hetero atoms such as nitrogen, oxygen or sulfur, particularly wherein the aromatic portion of such groups contain such hetero atom.

Examples of alpha-aminomethylene phosphonic acids which may be utilized in the reaction with an epoxy compound to prepare a compound of the invention include: (2-hydroxyethyl)aminobis(methylenephosphonic)acid, i.e., $HOCH_2CH_2N(CH_2PO_3H_2)_2$; isopropylaminobis(methylenephosphonic)acid, i.e., i-propylN$(CH_2PO_3H_2)_2$; n-propylaminobis(methylenephosphonic)acid, i.e., n-propylN$(CH_2PO_3H_2)_2$; n-butylaminobis(methylenephosphonic)acid, i.e., n-butylN$(CH_2PO_3H_2)_2$; n-hexylaminobis(methylenephosphonic)acid, i.e., n-hexylN$(CH_2PO_3H_2)_2$; (2-ethylhexyl)aminobis(methylenephosphonic)acid, i.e., (2-ethylhexyl)N$(CH_2PO_3H_2)_2$; n-octylaminobis(methylenephosphonic)acid, i.e., n-octylN$(CH_2PO_3H_2)_2$; isononylaminobis(methylenephosphonic)acid, i.e., isononylN$(CH_2PO_3H_2)_2$; dodecylaminobis(methylenephosphonic)acid, i.e., dodecylN$(CH_2PO_3H_2)_2$; diethylamino(methylenephosphonic)acid, i.e., $(CH_3CH_2)_2NCH_2PO_3H_2$; dimethylamino(methylenephosphonic)acid, i.e., $(CH_3)_2NCH_2PO_3H_2$; nitrilotris(methylenephosphonic)acid, i.e., $N(CH_2PO_3H_2)_3$; ethylenediaminetetrakis(methylenephosphonic)acid, i.e., $[CH_2N(CH_2PO_3H_2)_2]_2$; diethylenetriaminepentakis(methylenephosphonic)acid, i.e., $H_2O_3PCH_2N[CH_2CH_2N(CH_2PO_3H_2)_2]_2$; benzylaminobis(methylenephosphonic)acid; reaction products of phosphorous acid and formaldehyde with polyoxyalkylene polyamines and polyoxyalkylene monoamines (e.g., such polyamines and monoamines as available under the trademark, JEFFAMINE®, from Texaco, Inc.); as well as the products produced by reacting phosphorous acid, cocoamine, and formaldehyde (e.g., in a molar ratio of 2:1:2 respectively, as illustrated in Example 1 below for the preparation of cocoaminebis(methylenephosphonic) acid). Alpha-aminomethylene phosphonic acids are generally known compounds and can be prepared utilizing generally known methods. Many alpha-aminomethylene phosphonic acids are available commercially.

As set forth above, a compound of the invention is a reaction product of at least one phosphonic acid group of an alpha-aminomethylene phosphonic acid, preferably corresponding to the formula above, with an epoxy group of a compound containing at least one epoxy group, preferably with an epoxy group of a compound containing at least one 1,2-epoxy group. Hydroxyl groups may also be present in such epoxy compounds and often are. In general the epoxide equivalent weight of the epoxy compounds will range from 44 to about 4,000, typically from about 150 to about 500. The epoxy compounds may be saturated or unsaturated, cyclic or acyclic, aliphatic, alicyclic, aromatic or heterocyclic. They may contain substituents such as halogen, hydroxyl and ether groups.

Examples of epoxy compounds which may be utilized include compounds as simple as ethylene oxide, propylene oxide, butylene oxide, cyclohexene oxide, and the like.

Examples of epoxy compounds which may be utilized also include: the epoxy polyethers obtained by reacting an epihalohydrin (such as epichlorohydrin or epibromohydrin) with a polyphenol in the presence of an alkali. Suitable polyphenols include: 2,2-bis(4-hydroxyphenyl)propane (i.e., bisphenol-A), 1,1-bis(4-hydroxyphenyl)isobutane, 2,2-bis(4-hydroxytertiarybutylphenyl)propane, 4,4-dihydroxybenzophenone, 1,1-bis(4-hydroxyphenyl)ethane, bis(2-hydroxynaphthyl)methane, 1,5-dihydroxynaphthalene, 1,1-bis(4-hydroxy-3-allylphenyl)ethane, and the hydrogenated derivatives of such compounds. The polyglycidyl ethers of polyphenols of various molecular weights may be produced, for example, by varying the mole ratio of epichlorohydrin to polyphenol in known manner.

Examples of epoxy compounds which may be utilized also include: the polyglycidyl ethers of mononuclear polyhydric phenols such as the polyglycidyl ethers of resorcinol, pyrogallol, hydroquinone, and pyrocatechol, as well as the monoglycidyl ethers of monohydric phenols such as phenylglycidyl ether, alpha-naphthylglycidyl ether, beta-naphthylglycidyl ether, and the corresponding compounds bearing an alkyl substituent on the aromatic ring.

Examples of epoxy compounds which may be utilized also include: the glycidyl ethers of aromatic alcohols, such as benzylglycidyl ether and phenylglycidyl ether.

Examples of epoxy compounds which may be utilized also include: the polyglycidyl ethers of polyhydric alcohols such as the reaction products of epichlorohydrin or dichlorohydrin with aliphatic and cycloaliphatic alcohols such as ethylene glycol, diethylene glycol, triethylene glycol, dipropylene glycol, tripropylene glycol, propane diols, butane diols, pentane diols, glycerol, 1,2,6-hexanetriol, pentaerythritol and 2,2-bis(4-hydroxycyclohexyl)propane.

Examples of epoxy compounds which may be utilized also include: polyglycidyl esters of polycarboxylic acids such as the generally known polyglycidyl esters of adipic acid, phthalic acid, and the like. Other epoxy compounds which may be utilized include: the monoglycidyl esters of monocarboxylic acids, such as glycidyl benzoate, glycidyl naphthoate as well as the monoglycidyl esters of substituted benzoic acid and naphthoic acids.

Addition polymerized resins containing epoxy groups may also be employed. Such materials may be produced by the addition polymerization of epoxy functional monomers such as glycidyl acrylate, glycidyl methacrylate and allyl glycidyl ether typically in combination with ethylenically unsaturated monomers such as styrene, alpha-methyl styrene, alpha-ethyl styrene, vinyl toluene, t-butyl styrene, acrylamide, methacrylamide, acrylonitrile, methacrylonitrile, ethacrylonitrile, ethyl methacrylate, methyl methacrylate, isopropyl methacrylate, isobutyl methacrylate, hydroxyethyl acrylate, hydroxyethyl methacrylate, 2-ethylhexyl acrylate, 2-ethylhexyl methacrylate, isobornyl methacrylate, and the like.

Many additional examples of epoxy compounds are described in the *Handbook of Epoxy Resins*, Henry Lee and Kris Neville, 1967, McGraw Hill Book Company.

The relative proportions in which the alpha-aminomethylene phosphonic acid and the compound containing at least one epoxy group may be reacted together to form a compound of the invention may vary widely. However typically the amount of alpha-aminomethylene phosphonic acid and epoxy compound are chosen to provide a ratio of moles of epoxy groups to moles of replaceable hydrogens from the phosphonic acid group(s) in a range of from 1.0:8.0 to 1.0:1.0, usually from 1.0:4.0 to 1.0:1.0, and preferably 1.0:4.0. It also should be understood that in the case where the reactants are polyfunctional, the reaction product is likely to be a statistical mixture of a number of different molecular species. With respect to the preferred ratio of 1.0:4.0, it has been found that in some cases at lower levels of epoxy, the antigassing effect in a waterborne composition containing metallic pigment such as aluminum flakes and the humidity resistance of dry films from waterborne coating compositions incorporating the compound (reaction product) are not quite as good as at the aforesaid 1.0:4.0 ratio; and at higher levels of epoxy, while the humidity resistance is improved for dry films from the waterborne composition, the compounds effect as an antigassing agent in the waterborne composition containing metallic pigment is diminished somewhat.

The reaction of the alpha-aminomethylene phosphonic acid and the compound containing at least one epoxy group may be conducted at a temperature in the range, for example, of from 25 degrees Celsius (°C.) to about 150° C., typically in a range of from about 80° C. to about 100° C., and usually in a range of from about 85° C. to about 95° C. Where desired, a catalyst for opening an epoxy ring, for example a tertiary amine, may be employed in the reaction of the alpha-aminomethylene phosphonic acid and the epoxy compound, but typically such catalyst is not utilized in preferred embodiments of the invention. In order to maintain fluidity of the reaction mixture, especially where the epoxy compound is a relatively high-melting solid, it may be advantageous to conduct the reaction in an inert, polar diluent or solvent, such as 1-methoxy-2-propanol, dioxane, tetrahydrofuran and the like. Where a polar diluent or polar solvent is employed, the reaction can be conveniently carried out at the reflux temperature of the diluent or solvent.

It has been found that incorporation of a compound of the invention in a waterborne coating composition containing metallic pigment (one preferred embodiment of the invention) reduces or prevents gassing of the coating composition. It has also been found that a compound of the invention can be incorporated in such waterborne coating composition without disadvantageously affecting humidity resistance of dry films (coatings) produced from such waterborne composition. Moreover, it has been found that incorporation of a compound of the invention in a pigmented waterborne coating composition can provide enhanced resistance to pigment settling. A waterborne coating composition of the invention comprises a film-forming polymer, a metallic pigment, an aqueous diluent medium and a compound of the invention. The tendency of the pigment to react with the aqueous medium and release gaseous material is prevented or reduced by the incorporation of an effective amount of a compound of the invention therein. Typically for this embodiment of the invention, compounds of the invention prepared from alpha-aminomethylene phosphonic acids corresponding to the above formula in which a=2 and 1,2-epoxy group-containing diepoxides have been employed.

Although for a waterborne coating composition of the invention, the reaction product of the alpha-aminomethylene phosphonic acid and the compound containing at least one epoxy group may be employed directly as an antigassing agent, typically it will be utilized in a form in which the reaction product has been neutralized with ammonia or an amine such as N,N-dimethylethanolamine, triethylamine, or the like, for example where acidity of the reaction product in aqueous medium may affect stability of other constituents of the coating composition, in particular the film-forming polymer. For example, where the film-forming polymer is an addition polymer containing carboxylic acid groups which polymer is rendered soluble or dispersible in water by neutralization of the carboxylic acid groups with ammonia or an amine, the addition of unneutralized compound of the invention may tend to cause precipitation (flocculation) of the film-forming polymer.

Examples of metallic pigments for utilization in a waterborne coating composition of the invention include any metallic pigments which are generally known for use in pigmented waterborne coating compositions. Examples include metallic pigments, particularly metallic flake pigments, composed of aluminum, copper, zinc and/or brass as well as those composed of other malleable metals and alloys such as nickel, tin, silver, chrome, aluminum-copper alloy, aluminum-zinc alloy, and aluminum-magnesium alloy. Of the aforesaid examples, aluminum flake pigment is preferred. Moreover, a waterborne coating composition of the invention may also include, and typically does include, one or more of a wide variety of other pigments generally known for use in coating compositions such as various white and colored pigments. Examples of white and colored pigments include generally known pigments based on metal oxides; metal hydroxides; metal sulfides; metal sulfates; metal carbonates; carbon black; china clay; phthalo blues and green, organo reds, and other organic dyes.

Various procedures may be used for incorporating a compound of the invention into a waterborne coating composition of the invention. One method is to bring the metallic pigment into contact with the compound of the invention prior to the incorporation of the pigment into the waterborne coating composition. This may be done by adding the compound of the invention to the pigment paste (e.g., pigment as normally supplied commercially), or it may be added at an earlier stage such as during the actual production of the pigment. Alternatively, a compound of the invention may be introduced into a waterborne coating composition of the invention by simply introducing it as a further ingredient in the formulation of the waterborne coating composition, for example during the mixing of film-forming resin, metallic pigment and aqueous medium together with other conventional and optional constituents such as crosslinking agents, co-solvents, thickeners and fillers. Irrespective of the manner in which a compound of the invention is incorporated into a waterborne coating composition of the invention, an amount of such compound generally is employed which is effective in reducing or eliminating gassing of the metallic pigment in the aqueous medium. Typically an amount of from 0.50 percent to 25.0 percent by weight, usually from 5.0 percent to 15.0 percent by weight, based on the weight of metallic pigment (e.g., aluminum flake) utilized in the waterborne composition, is employed for this purpose.

A waterborne coating composition of the invention may contain, as the film-forming polymer, any polymer or polymers generally known for use in waterborne coating compositions. Examples include polymers solubilized or dispersed in aqueous medium, for example via neutralization with ammonia or an amine of carboxylic acid groups which such polymers may contain, some examples of which include water solubilized or water dispersed, acrylics, urethanes, polyesters, epoxies, aminoplasts or mixtures thereof. Such film-forming polymers can be employed optionally in combination with various ingredients generally known for use in waterborne coating compositions containing film-forming polymers of these general classes. Examples of these various ingredients include: fillers; plasticizers; antioxidants; mildewcides and fungicides; surfactants; various flow control agents including, for example, thixotropes and additives for sag resistance and/or pigment orientation such as precipitated silicas, fumed silicas, organo-modified silicas, bentone clays, organo-modified bentone clays, and such additives based on polymer microparticles (sometimes referred to as microgels) described for example in U.S. Pat. Nos. 4,025,474; 4,055,607; 4,075,141; 4,115,472; 4,147,688; 4,180,489; 4,242,384; 4,268,547; 4,220,679; and 4,290,932 the disclosures of which are hereby incorporated by reference.

Incorporation of a compound of the invention in an organic solvent-borne coating composition comprising a film-forming polymer, a metallic pigment and an organic solvent and/or organic diluent medium can reduce gassing of the coating composition which can occur with the introduction of moisture, for example, from various pigments which have not been dried thoroughly before incorporation in the coating composition, or for example from atmospheric moisture which sometimes can slowly enter a storage container for the coating composition over time. It has also been found that incorporation of a compound of the invention in an organic solvent-borne coating composition additionally comprising an organic coloring pigment which tends to result in a color drift of the coating composition over time, can increase the color stability of such a solvent-borne coating composition. In a presently preferred embodiment of the invention, a compound of the invention utilized for this purpose is prepared using a compoud containing one 1,2-epoxy group. Without intending to be bound thereby, it is believed that incorporation of a compound of the invention in an organic solvent-borne coating composition additionally containing organic coloring pigment (e.g., Carbazole violet as obtained from GAF Corp.) helps prevent agglomeration of the metallic pigment (e.g., Al flake) and/or agglomeration of the metallic pigment with other pigments, for example coloring pigments, in the solvent-borne coating composition.

Examples of metallic pigments for utilization in an organic solvent-borne coating composition of the invention include any metallic pigments which are generally known for use in pigmented organic solvent-borne coating compositions. Examples include metallic pigments, particularly metallic flake pigments, as set forth in the preceding description of metallic pigments for utilization in waterborne coating compositions of the invention. Of the aforesaid examples, aluminum flake pigment is preferred. Additionally, an organic solvent-borne coating composition of the invention may also include, and typically does include, one or more of a wide variety of other pigments generally known for use in coating compositions such as various white and colored pigments. Examples of white and colored pigments include the generally known pigments set forth previously in the description of white and colored pigments for utilization in a waterborne coating composition of the invention. As for a waterborne coating composition, various procedures may be used for incorporating a compound of the invention into an organic solvent-borne coating composition of the invention such as, for example, bringing the pigment into contact with the compound of the invention prior to the incorporation of the pigment into the organic solvent-borne coating composition via addition to the pigment paste, or during the actual production of the pigment, or by introduction of the compound of the invention directly as a further ingredient in the formulation of the organic solvent-borne coating composition, for example via mixing of film-forming resin, pigment and organic medium together with other conventional and optional constituents such as crosslinking agents, co-solvents, thickeners and fillers. Irrespective of the manner in which a compound of the invention is incorporated into an organic solvent-borne coating composition of the invention, an amount of such compound generally is employed which is effective in reducing or eliminating gassing over time of an organic solvent-borne coating composition containing metallic pigment. Typically an amount of from 0.10 percent to 15.0 percent by weight, usually from 2.0 percent to 8.0 percent by weight, based on the weight of metallic flake pigment (e.g., aluminum flake) utilized, is employed for this purpose. Where a coloring pigment which tends to cause a color drift of the coating composition over time is employed in the coating composition, an amount of such compound generally is employed which is effective in stabilizing the organic solvent-borne coating composition against such color change. Typically an amount of from 0.10 percent to 15.0 percent by weight, usually from 2.0 percent to 8.0 percent by weight, based on the weight of metallic flake pigment (e.g., aluminum flake) utilized, is employed for this purpose.

An organic solvent-borne coating composition of the invention may contain, as the film-forming polymer, any polymer or polymers generally known for use in organic solvent-borne coating compositions. Examples include, acrylics, urethanes, polyesters, epoxies, aminoplasts or mixtures thereof. Such film-forming polymers can be employed optionally in combination with various ingredients generally known for use in organic solvent-borne coating compositions containing film-forming polymers of these general classes. Examples of these various ingredients include: fillers; plasticizers; antioxidants; mildewcides and fungicides; surfactants; various flow control agents including, for example, thixotropes and additives for sag resistance and/or pigment orientation such as precipitated silicas, fumed silicas, organo-modified silicas, bentone clays, organo-modified bentone clays, and such additives based on polymer microparticles described for example in U.S. Pat. Nos. 4,025,474; 4,055,607; 4,075,141; 4,115,472; 4,147,688; 4,180,489; 4,242,384; 4,268,547; 4,220,679; and 4,290,932 which have been incorporated by reference herein.

Examples of organic solvents and/or diluents which may be employed in an organic solvent-borne coating composition of the invention include: alcohols such as lower alkanols containing 1 to 8 carbon atoms including methanol, ethanol, n-propanol, isopropanol, butanol, sec-butyl alcohol, tertbutyl alcohol, amyl alcohol, hexyl alcohol and 2-ethylhexyl alcohol; ethers and ether alcohols such as ethyleneglycol monoethyl ether, ethyleneglycol monobutyl ether, ethyleneglycol dibutyl ether, propyleneglycol monomethyl ether, diethyleneglycol monobutyl ether, diethyleneglycol dibutyl ether, dipropyleneglycol monomethyl ether, and dipropyleneglycol monobutyl ether; ketones such as methyl ethyl ketone, methyl isobutyl ketone, methyl amyl ketone and methyl N-butyl ketone; esters such as butyl acetate, 2-ethoxyethyl acetate and 2-ethylhexyl acetate; aliphatic and alicyclic hydrocarbons such as the various petroleum naphthas and cyclohexane; and aromatic hydrocarbons such as toluene and xylene. The amount of organic solvent and/or diluent utilized in an organic solvent-borne coating composition of the invention may vary widely. However, typically the amount of organic solvent and/or diluent can range from about 10 percent to about 50 percent, usually from about 20 percent to about 40 percent, by weight based on the total weight of organic solvent-borne coating composition.

It has also been found that compounds of the invention can provide particular advantages in powder coating compositions comprising a film-forming polymer and a pigment. For example, it has been found that dispersibility of pigment in such powder coating compositions is improved by incorporating therein an effective amount of a compound of the invention. Such improved pigment dispersion can provide advantages such as improved uniformity of color, improved hiding, improved gloss, improved definition of image (DOI), and improved flow and leveling of the powder coating composition upon heating.

The following examples illustrate the invention and should not be construed as a limitation on the scope thereof. Unless specifically indicated otherwise, all percentages and amounts are understood to be by weight. Wherever used herein "pbw" means parts by weight.

EXAMPLE 1

This example illustrates the preparation of cocoamine bis(methylenephosphonic)acid and its reaction with the diglycidyl ether of bisphenol-A to prepare a compound of the invention.

A solution containing 98.0 grams (g) of phosphorous acid (1.19 mole) and 75.0 g of 1-methoxy-2-propanol is heated to 85° C. under a nitrogen atmosphere. Next, 130.0 g of cocoamine (0.66 mole, available as AR-MEEN CD ® and having an amine equivalent weight of 196) and 98.0 g of a 37 percent by weight solution of formaldehyde in water (1.20 mole formaldehyde) are added simultaneously as separate feeds over 1.5 hours to this solution. The resulting reaction mixture is held for 4 hours at reflux temperature (98°-100° C.), whereupon a mixture containing 116.2 g of bisphenol-A diglycidyl ether (0.30 mole, available as EPON ® 828 from Shell Chemical Co.) and 30.0 g of 1-methoxy-2-propanol is added over 1 hour, after which the reaction mixture is held at reflux for 1.5 hours. The resulting product is cooled to 60° C. and then neutralized by the addition of 55.0 g of N,N-dimethylethanolamine (0.62 mole) over 15 minutes after which the resulting product is allowed to cool to room temperature. The resulting product, which contains a compound of the invention, has a Gardner-Holdt bubble tube viscosity of X, a total solids content of 67 percent by weight, and a pH of 5.35.

EXAMPLE 2

This example illustrates the preparation of cocoamine bis(methylenephosphonic)acid and its reaction with phenyl glycidyl ether to prepare a compound of the invention.

A solution containing 864.6 g of phosphorous acid (10.54 mole) and 1440.2 g of 1-methoxy-2-propanol is heated to 85° C. under a nitrogen atmosphere. Next, 1036.0 g of cocoamine (ARMEEN CD ®, 5.28 mole) and 840.0 g of a 37 percent by weight solution of formaldehyde in water (10.35 mole formaldehyde) are added simultaneously as separate feeds over 1.5 hours to this solution. The resulting reaction mixture is held for 4 hours at 100° C. (reflux temperature), thereafter cooled to 85° C. after which 790.0 g of phenyl glycidyl ether (5.26 mole) is gradually added over 1 hour. The resulting reaction mixture is held at 85° C. for 3 hours, thereafter cooled to less than 60° C., and then neutralized by the addition of 467.0 g of N,N-dimethylethanolamine (0.5.24 mole) over 30 minutes. The resulting product, which contains a compound of the invention, is vacuum stripped to produce a product having a Gardner-Holdt bubble tube viscosity of Z-4/Z-5, a total solids content of 83.9 percent by weight, and a pH of 5.05.

EXAMPLE 3

This example illustrates the preparation of cocoamine bis(methylenephosphonic)acid and its reaction with the diglycidyl ether of bisphenol-A to prepare a compound of the invention.

A solution containing 135.0 g of phosphorous acid (1.65 mole) and 225.0 g of 1-methoxy-2-propanol is heated to 85° C. under a nitrogen atmosphere. Next, 161.9 g of cocoamine (ARMEEN CD ®, 0.83 mole) and 131.3 g of a 37 percent by weight solution of formaldehyde in water (1.62 mole formaldehyde) are added simultaneously as separate feeds over 1.5 hours to this solution. The resulting reaction mixture is held for 5 hours at 100° C., thereafter cooled to 60° C., and then neutralized with a solution of 73.3 g of N,N-dimethylethanolamine (0.82 mole) in 50.0 g of 1-methoxy-2-propanol. A mixture containing 155.5 g of bisphenol-A diglycidyl ether (EPON 828 ®, 0.41 mole) and 50.0 g of 1-methoxy-2-propanol is added, and the resulting reaction mixture is heated to 100° C., held at this temperature for 5 hours, and thereafter cooled to room temperature. The resulting product, which contains a compound of the invention, is a homogeneous liquid with a Gardner-Holdt bubble tube viscosity of 0 and has a total solids content of 56.7 percent by weight.

EXAMPLE 4

This example illustrates the preparation of cocoamine bis(methylenephosphonic)acid and its reaction with phenyl glycidyl ether to prepare a compound of the invention.

A solution containing 135.0 g of phosphorous acid (1.65 mole) and 225.0 g of 1-methoxy-2-propanol is heated to 85° C. under a nitrogen atmosphere. Next, 161.9 g of cocoamine (ARMEEN CD ®, 0.83 mole) and 131.3 g of a 37 percent by weight solution of formaldehyde in water (1.62 mole formaldehyde) are added simultaneously as separate feeds over 1.5 hours to this solution. The resulting reaction mixture is held for 5 hours at 100° C., thereafter cooled to 60° C., and then neutralized with 73.3 g of N,N-dimethylethanolamine (0.82 mole). Next, 123.5 g of phenyl glycidyl ether (0.82 mole) is added; the resulting reaction mixture is heated to 100° C. and held at this temperature for 5 hours; and thereafter cooled. The resulting product, which contains a compound of the invention, is vacuum stripped to remove solvent and water to produce a product having a Gardner-Holdt bubble tube viscosity of Z-5 and a total solids content of 82.2 percent by weight.

EXAMPLE 5

In this example a method known as the "Borax Test" disclosed in U.S. Pat. No. 4,693,754 is used to evaluate the effectiveness of antigassing agents for the protection of aluminum flake pigment in a waterborne composition from reaction with water. The "Borax Test" provides an accelerated testing method whereby aluminum flake pigment paste is incorporated in a water solution which is 0.024 Molar in $Na_2B_4O_7$ and 0.002 Molar in NaOH (NaOH is added to adjust the pH to 9.26). The solution is heated in a constant temperature bath at 140° F. (60° C.) and the rate of hydrogen gas evolved is recorded. An antigassing agent of the invention is added to the waterborne composition containing the aluminum flake (Composition A below) and its relative effectiveness is evaluated by comparing the rate of hydrogen evolution to that from comparative compositions which are the same except for the substitution in one comparative composition of a known antigassing agent (an organic ester of orthophosphoric acid) prepared substantially according to Example 1 of U.S. Pat. No. 4,621,112 (Composition B below) and the use in the other comparative composition of no antigassing agent (Composition C below). (The aforesaid known antigassing agent is prepared according to Example 1 of U.S. Pat. No. 4,621,112 except for the substitution of diisopropanolamine for triethylamine as neutralizing agent and substitution of 1-methoxy-2-propanol for tetrahydrofuran as solvent in the synthesis.)

The components of the aforesaid compositions A, B and C are as set forth in the following Table 1.

TABLE 1

| Composition | Al Paste[1] | Antigassing Agent | 1-Methoxy-2-propanol | Borate Solution[2] |
|---|---|---|---|---|
| A | 15.38 g | 1.67 g[3] | 20 ml (milliliters) | 25 ml |
| B | 15.38 g | 2.38 g[4] | 20 ml | 25 ml |
| C | 15.38 g | None | 20 ml | 25 ml |

[1] A 65.0 percent by weight solids aluminum flake pigment paste in mineral spirits and oleic acid (available as 7575 FG Aluminum Paste from Silberline Manufacturing Co.)
[2] A solution containing 0.024 moles/liter of $Na_2B_4O_7$ and 0.002 moles/liter of NaOH in deionized water.
[3] The resulting product of example 3 above (containing compound of the invention) reduced to 30 percent by weight solids in 1-methoxy-2-propanol and water.
[4] The known antigassing agent prepared substantially according to Example 1 of U.S. Pat. No. 4,621,112 at 21 percent by weight solids in 1-methoxy-2-propanol and water.

Compositions A, B and C are placed separately in flasks; each flask is sealed with a rubber stopper, and immediately placed in a constant temperature bath heated to 140° F. (60° C.). The hydrogen gas which is evolved is allowed to escape through a hole in the stopper into an inverted buret filled with water. The volume of gas given off, as shown by displacement of water in the buret, is then recorded at intervals over 24 hours with allowance made for expansion due to heating the flask and solution. The results at 5 hours and 24 hours are as summarized in the following Table 2. The values for milliliters of hydrogen gas evolved set forth in Table 2 are average values for three separate experimental runs for each composition. This is done to verify reproducibility. In Table 2, the symbol ">" means "greater than".

TABLE 2

| Milliliters (ml) of Hydrogen Gas Evolved | | |
|---|---|---|
| Composition | 5 Hours | 24 Hours |
| A | 0 | 1 |
| B | 17.7 | >50 |
| C | 34.2 | >50 |

As can be seen from the results summarized in Table 2 above, the metallic pigmented, waterborne composition A, containing a compound of the invention as antigassing agent, exhibits substantially less gassing than either composition B (containing the organic ester of orthophosphoric acid as antigassing agent prepared substantially according to Example 1 of U.S. Pat. No. 4,621,112) or composition C (containing no antigassing agent).

EXAMPLE 6

Solution acrylic polymers in organic solvents which also contain inorganic pigments, organic pigments (especially pigment such as carbazole violet) and aluminum pigments have long been known to be prone to color instability and pigment agglomeration. This condition is aggravated by the addition of water and upon heat aging. In this example 6, a solvent-borne acrylic lacquer coating composition (available as DURACRYL ® DBC-3704 from PPG Industries, Inc.) is used for evaluating the ability a compound of the invention (the product of Example 4 above) to alleviate the detrimental interactions associated with coatings containing certain pigments and aluminum flake as noted above.

The product of Example 4 above (containing compound of the invention) is incorporated into the solvent-borne acrylic lacquer coating composition by slurrying the product (at a level of 5 percent by weight based on the weight of aluminum solids) with the aluminum pigment paste prior to formulation into the DURACRYL ® DBC-3704 coating composition. Test samples 1 through 4 (as set forth in the following Table 3) are prepared to which are added 0 percent or 2 percent water on solution weight and which contain either 0 percent or 5 percent by weight of the product of Example 4 above based on the weight of aluminum flake solids as summarized in Table 3.

TABLE 3

| DURACRYL ® DBC-3704 coating composition containing: | | |
|---|---|---|
| | (Percent by weight Product of Ex. 4 based on Al flake solids) | (Percent by weight water Based on solution) |
| Sample 1 | 0 | 0 |
| Sample 2 | 0 | 2 |
| Sample 3 | 5 | 0 |
| Sample 4 | 5 | 2 |

Draw-downs (wet films) are prepared of each sample with a 3 mil Bird drawdown bar on Leneta paper as control for comparison to aged samples. The samples are divided in two, and half retained for room temperature aging while the remainder of each sample is sealed in a separate can for heat aging at 120° F. (48.9° C.). Drawdowns of each aged sample are made periodically over a 5 week period and evaluated relative to the control for color shift and pigment agglomeration. The results are as summarized in the following Table 4. Agglomeration is evidenced by the appearance of small lumps upon visual inspection. As used in the following Table 4, "Sl.Ag." means "Slight Agglomeration", "Sev.Ag." means "Severe Agglomeration", "+C.S." means that a positive change in color of the sample has occurred, and "N.C." means no agglomeration and no color change from the Control.

TABLE 4

| | Appearance of Films (Drawdowns) Prepared From Aged Coating Composition | | | |
| --- | --- | --- | --- | --- |
| | Room Temperature | | 120 Degrees F. | |
| Sample | 2 Weeks | 5 Weeks | 2 Weeks | 5 Weeks |
| 1 | Sl.Ag. | Sev.Ag. | Sl.Ag. | Sev.Ag. |
| 2 | Sl.Ag. | Sev.Ag. | Sl.Ag. + C.S. | Sev.Ag. + C.S. |
| 3. | N.C. | N.C. | N.C. | N.C. |
| 4. | N.C. | N.C. | N.C. | N.C. |

As is evident from the results summarized in Table 4 above, the color stability and resistance to pigment agglomeration in the DURACRYL® DBC-3704 coating composition are greatly improved by the addition of the product of Example 4 (according to the invention).

What is claimed is:

1. A waterborne coating composition comprising a film-forming polymer, a metallic pigment and an aqueous diluent medium, wherein the tendency of the pigment to react with the aqueous medium and release gaseous material is prevented or reduced by the incorporation in said coating composition of an effective amount of a compound which is a reaction product of at least one phosphonic acid group of an alpha-aminomethylene phosphonic acid containing at least one group corresponding to the formula,

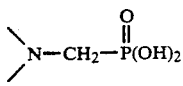

with an epoxy group of a compound containing at least one epoxy group.

2. The waterborne coating composition of claim 1 wherein said alpha-aminomethylene phosphonic acid corresponds to the formula,

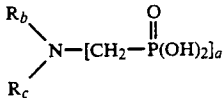

wherein
a = 1, 2 or 3,
a + b + c = 3,
and each R, which may be the same or different, is selected from the group consisting of alkyl, aryl, alkaryl, aralkyl and a monovalent residue of a polyether compound.

3. The waterborne coating composition of claim 1 wherein said metallic pigment comprises an aluminum pigment.

4. The waterborne coating composition of claim 3 wherein said metallic pigment comprises an aluminum pigment and said epoxy group is a 1,2-epoxy group.

5. The waterborne coating composition of claim 2 wherein a = 2 in said formula, said metallic pigment comprises an aluminum pigment and said epoxy group is a 1,2-epoxy group.

6. The waterborne coating composition of claim 5 wherein said compound containing at least one epoxy group is a diepoxide.

7. An organic solvent-borne coating composition comprising a film-forming polymer, a metallic pigment, an organic solvent medium, and a compound which is a reaction product of at least one phosphonic acid group of an alpha-aminomethylene phosphonic acid containing at least one group corresponding to the formula,

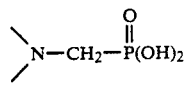

with an epoxy group of a compound containing at least one epoxy group.

8. The organic solvent-borne coating composition of claim 7 wherein said alpha-aminomethylene phosphonic acid corresponds to the formula,

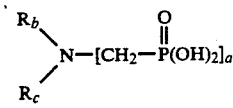

wherein
a = 1, 2 or 3,
a + b + c = 3,
and each R, which may be the same or different, is selected from the group consisting of alkyl, aryl, alkaryl, aralkyl and a monovalent residue of a polyether compound.

9. The organic solvent-borne coating composition of claim 7 wherein said metallic pigment comprises an aluminum pigment.

10. The organic solvent-borne coating composition of claim 7 wherein said epoxy group is a 1,2-epoxy group.

11. The organic solvent-borne coating composition of claim 7 comprising an organic coloring pigment wherein the color stability of said solvent-borne coating composition is increased by incorporation therein of an effective amount of said reaction product.

12. The organic solvent-borne coating composition of claim 8 wherein a = 2 in said formula.

13. The organic solvent-borne coating composition of claim 12 wherein said compound containing at least one epoxy group is a monoepoxide.

14. A powder coating composition comprising a film-forming polymer and a pigment, wherein dispersibility of said pigment in said powder coating composition is improved by incorporating therein an effective amount of a compound which is a reaction product of at least one phosphonic acid group of an alpha-aminomethylene phosphonic acid containing at least one group corresponding to the formula,

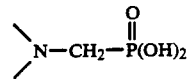

with an epoxy group of a compound containing at least one epoxy group.

15. The powder coating composition of claim 14 wherein said alpha-aminomethylene phosphonic acid corresponds to the formula,

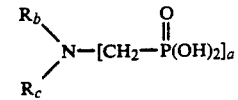

wherein $a = 1$, 2 or 3, $a + b + c = 3$, and each R, which may be the same or different, is selected from the group consisting of alkyl, aryl, alkaryl, aralkyl and a monovalent residue of a polyether compound.

16. The powder coating composition of claim 15 wherein said epoxy group is a 1,2-epoxy group.

* * * * *